United States Patent [19]

Wright

[11] Patent Number: 5,147,335
[45] Date of Patent: Sep. 15, 1992

[54] TRANSURETHROVESICAL BIOPSY, AMNIOCENTESIS AND BIOLOGICAL SAMPLING GUIDE

[75] Inventor: Jeffrey Wright, San Antonio, Tex.

[73] Assignee: Board of Regents, The University of Texas System, Austin, Tex.

[21] Appl. No.: 398,848

[22] Filed: Aug. 24, 1989

[51] Int. Cl.$^5$ ............................................. A61M 25/00
[52] U.S. Cl. .................................. 604/280; 604/164; 604/264; 604/55; 128/763
[58] Field of Search ....................... 604/27, 28, 51, 55, 604/264, 280, 116, 164; 128/753, 754, 760, 763

[56] References Cited

U.S. PATENT DOCUMENTS

| | | | |
|---|---|---|---|
| 3,804,097 | 4/1974 | Rudie | 128/350 |
| 4,037,599 | 7/1977 | Raulerson | 128/214.4 |
| 4,073,297 | 2/1978 | Kopp | 128/214.4 |
| 4,096,860 | 6/1978 | McLaughlin | 128/214.4 |
| 4,134,402 | 1/1979 | Mahurkar | 604/272 |
| 4,308,875 | 1/1982 | Young | 128/753 |
| 4,403,983 | 9/1983 | Edelman et al. | 604/43 |
| 4,447,235 | 5/1984 | Clarke | 604/169 |
| 4,568,329 | 2/1986 | Mahurkar | 604/280 |
| 4,583,968 | 4/1986 | Mahurkar | 604/280 |
| 4,601,701 | 7/1986 | Mueller, Jr. | 604/83 |
| 4,619,643 | 10/1986 | Bai | 604/43 |
| 4,626,240 | 12/1986 | Edelman et al. | 604/43 |
| 4,808,155 | 2/1989 | Mahurkar | 604/280 |
| 4,842,582 | 6/1989 | Mahurkar | 604/280 |
| 4,850,373 | 7/1989 | Zatloukal et al. | 128/253 |
| 4,935,008 | 6/1990 | Lewis, Jr. | 604/164 |

OTHER PUBLICATIONS

J. Parsons, et al., "Oocyte Retrieval for in-v itro Fertilization by Ultrasonically Guided Needle Aspiration Via the Urethra" The Lancet, May 11, 1985, pp. 1076–1077.

W. Butler, et al., "In Vitro Fertilization and Birth After Ultrasonically Guided Transurethral Aspiration of Oocytes", Southern Medical Journal vol. 80, No. 5 (May 1987), pp. 659–662.

*Primary Examiner*—Stephen C. Pellegrino
*Assistant Examiner*—Michael Rafa
*Attorney, Agent, or Firm*—Arnold, White & Durkee

[57] ABSTRACT

A metehod and device for transurethrovesical biopsies, amnioceenteses and other biological sampling procedures utilizing a double lumen catheter is achieved by the present invention. The catheter includes a rigid lumen to guide a needle and a second lumen able to pass fluid. In transurethrovesical sampling procedures, the catheter is positioned across the bladder with one end of the catheter against the bladder wall which adjoins the uterus wall. Fluids pass through the second lumen to fill the bladder and increase sonographic visibility allowing the user better visibility for precise placement of the catheter. Preferably, an amniocentesis or biopsy needle is passed through the first rigid lumen, through the bladder wall, through the uterus wall and into the amniotic sac to allow withdrawal of amniotic fluid or other biological sample. The needle may then be withdrawn through the rigid lumen and the catheter removed. In other biosampling procedures, the catheter is positioned across a body cavity to permit filling the cavity with fluid, sampling the target and sonographically viewing the biosampling operation.

10 Claims, 3 Drawing Sheets

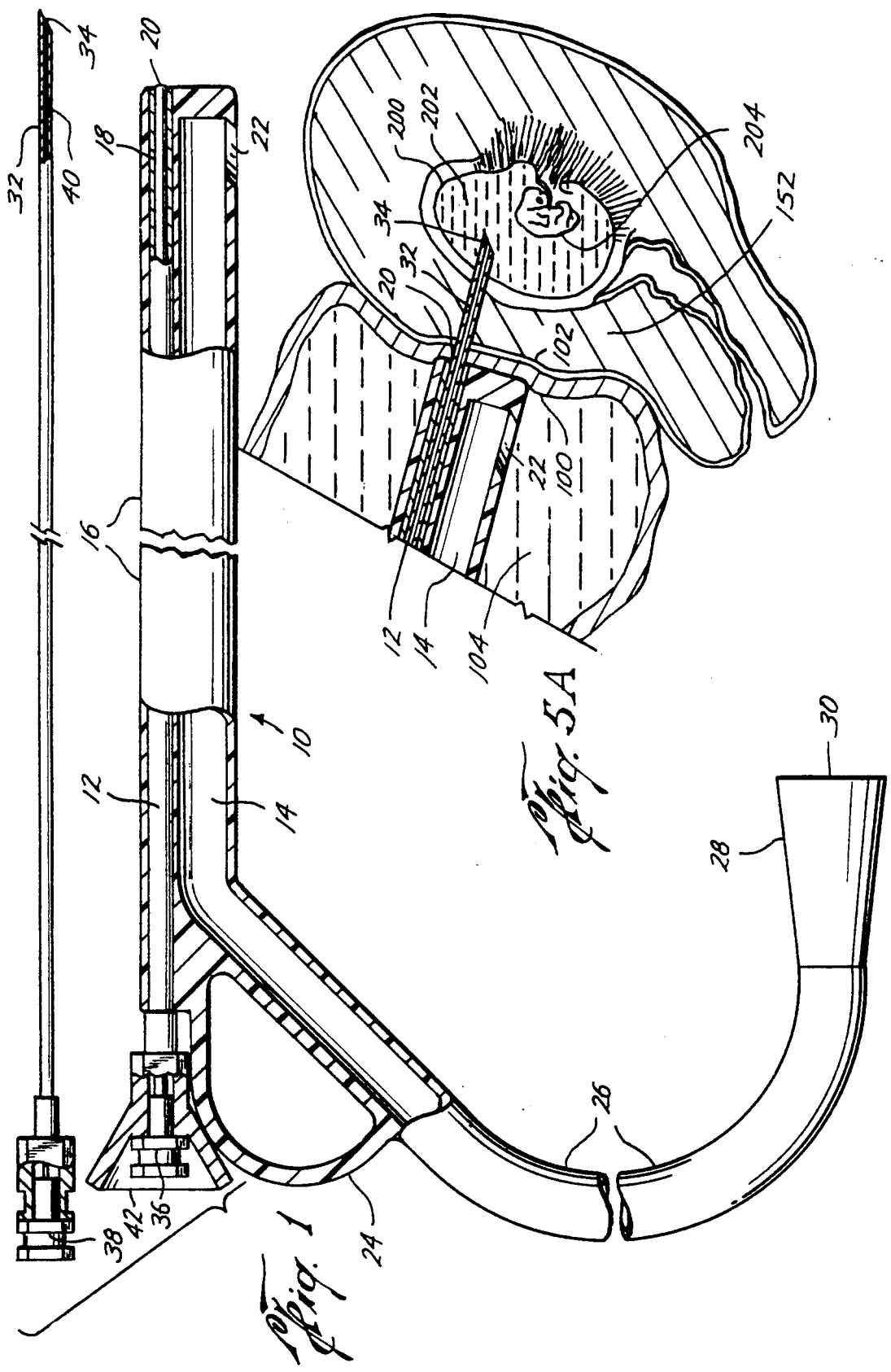

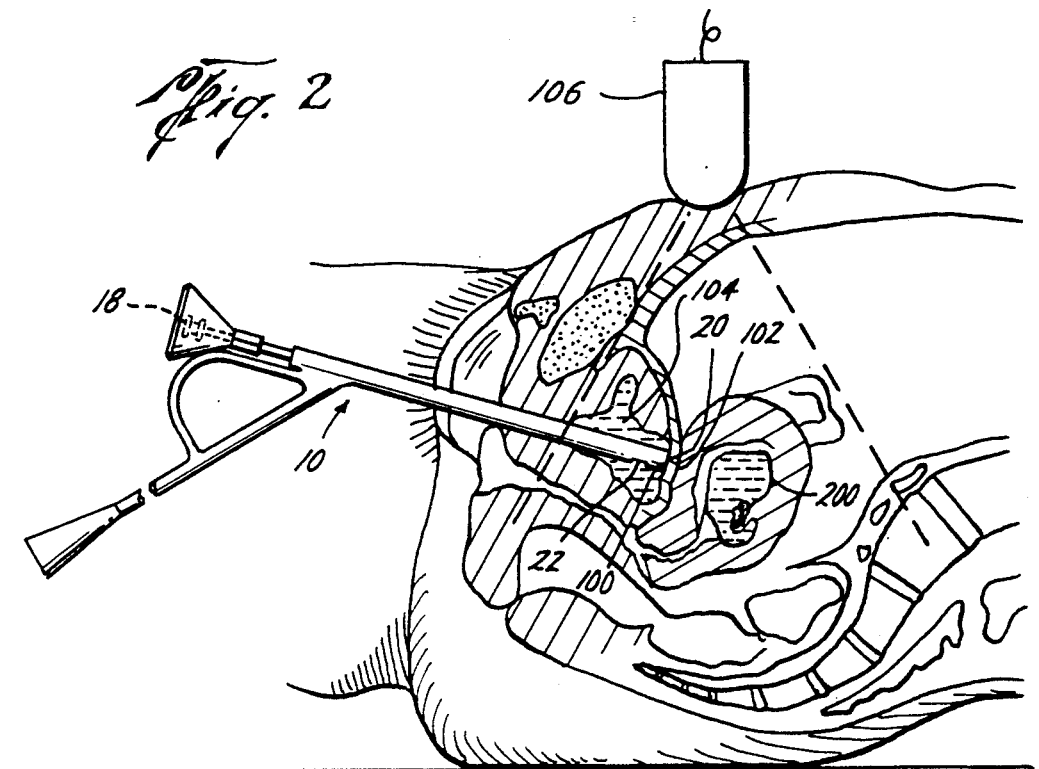
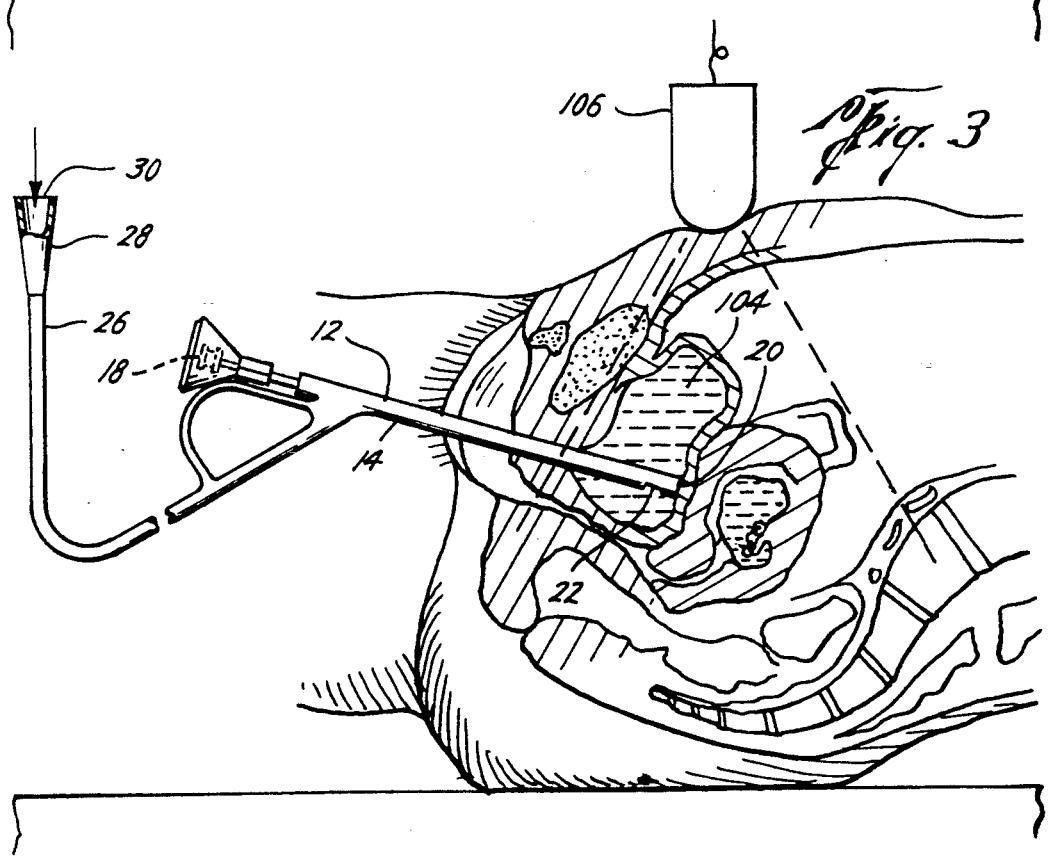

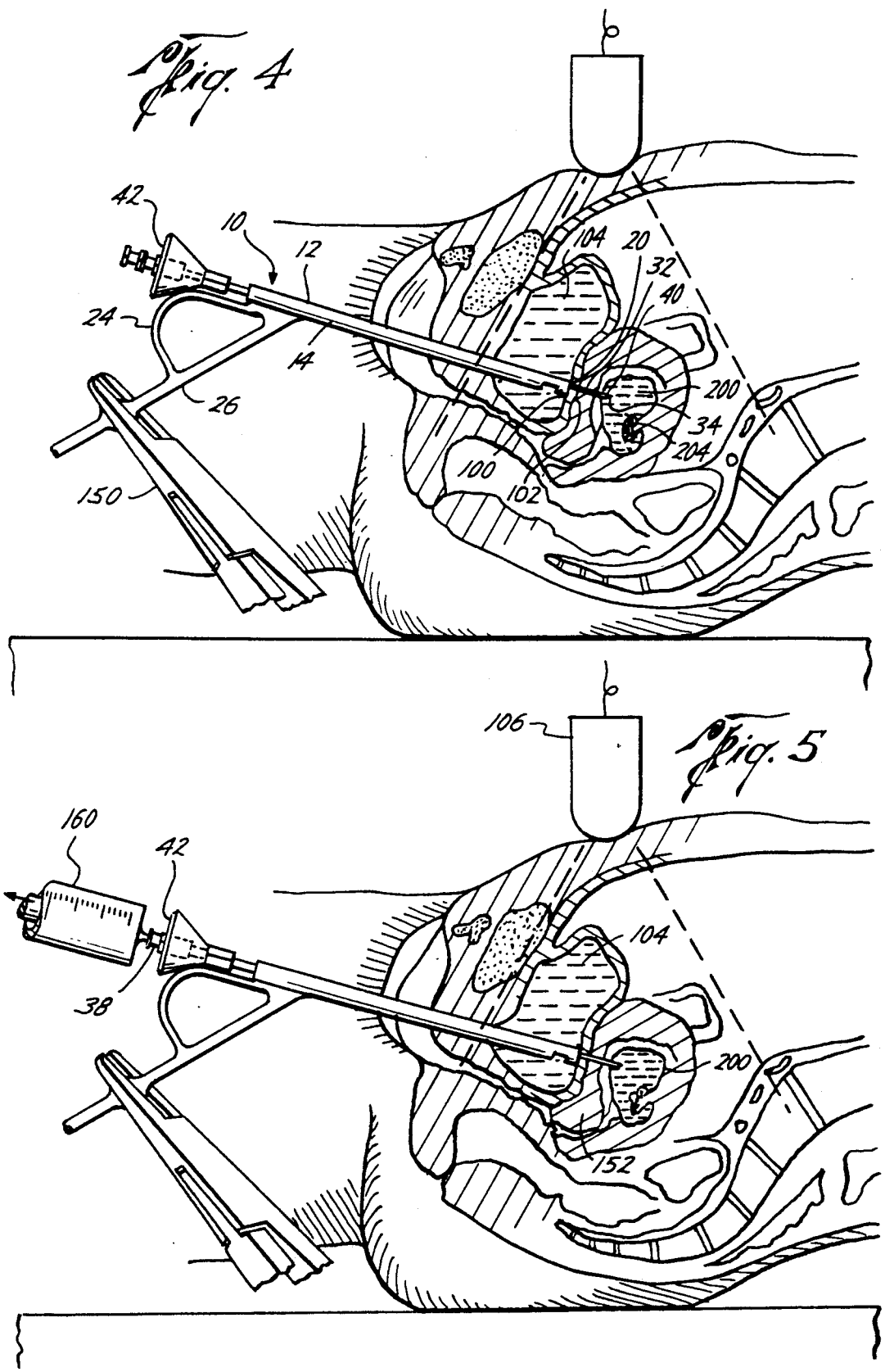

TRANSURETHROVESICAL BIOPSY, AMNIOCENTESIS AND BIOLOGICAL SAMPLING GUIDE

BACKGROUND OF THE INVENTION

The invention in a broad aspect relates to a multi-lumen catheter and a method for using the catheter for performing transurethrovesical biopsies, amniocenteses and other biological sampling procedures. More particularly, the invention provides for filling a bladder or other body cavity with a solution to increase sonographic visibility, during sonographic monitoring, and guiding a needle through the bladder or other cavity to accomplish a biopsy, amniocentesis or other biological sampling procedure.

Conventional amniocentesis is performed by passing an amniocentesis needle through the abdominal wall to gain access to the amniotic sac. Care must be exercised when passing the needle to avoid misguidance of the needle resulting in injury to the mother or fetus.

Because X-ray imaging may damage the fetus, the preferred imaging method to aid in guiding the amniocentesis needle is sonographic. Typically, a sonographic transducer is positioned to allow observation of the amniotic sac and the amniocentesis needle as the needle approaches and enters the amniotic sac. When a sonographic image is made through a cavity, the quality of the image, referred to as sonographic visibility, is improved when the cavity is filled with a fluid, preferably a liquid, rather than merely air.

The problems associated with traditional amniocentesis include, but are not limited to, risks of infection resulting if a piece of bowel is inadvertently pierced by the amniocentesis needle or infection resulting from the needle passing through the skin of the mother. A further complication may occur where the mother is significantly overweight producing difficulties in positioning the amniocentesis needle.

Because amniocentesis is currently being performed as early as eight to nine weeks into gestation, high precision in positioning and guiding the amniocentesis needle during insertion and sampling is required to avoid contacting or damaging the small fetus Increased sonographic visibility and a positionable guide for the amniocentesis needle can reduce the risks associated with amniocentesis. Increased visibility and a positionable guide can also reduce risks, such as risk of infection, associated with other biosampling procedures including, but not limited to transurethrovesical biopsies. Biosampling, as used throughout this application, means the obtaining of a biological sample, including but not limited to, a biological sample of an internal organ or a bodily fluid.

SUMMARY OF THE INVENTION

The present invention provides a device and method for transurethrovesical biopsies, amniocenteses, chorionic villus sampling and other biological sampling procedures. The invention allows for increased sonographic visibility while further providing a guide for needles, including but not limited to amniocentesis and biopsy needles. Generally speaking, the invention includes a multi-lumen catheter having a rigid guide lumen in which a needle may be inserted and a second lumen through which fluid may be passed. The catheter may be inserted across a body cavity and fluid may be inserted through the second lumen to fill the cavity and increase sonographic visibility. The catheter has a first or proximal end and a second or distal end. The terms "proximal" and "distal" in this context are intended to mean relative distances from a person using the catheter.

The multi-lumen catheter of the present invention comprises a first, rigid lumen having a first end and a second end where the first end has a first, proximal orifice for receiving a needle and the second end has a second, distal orifice allowing the needle to exit the second end of the first lumen. The second lumen has a fluid inlet end and a fluid outlet end. The first lumen is attached to the second lumen in a parallel relationship such that the first and second ends of the first lumen are in proximal relation to the fluid inlet and outlet ends of the second lumen, respectively. The first lumen is preferably able to receive common sizes of amniocentesis and biopsy needles, and the wall of the first rigid lumen is resistant to piercing by such needles The first lumen is preferably rigid and comprised of stainless steel or a rigid plastic.

The fluid inlet end of the second lumen is connectable to an inlet tube or other source of fluid. A system is provided for restricting the flow of fluid through the second lumen The fluid outlet end is preferably positioned aside the second lumen. The fluid outlet preferably allows a laminar flow of fluid from the fluid inlet through the second lumen. The fluid outlet is preferably in the range of approximately 4 to 8 square millimeters in cross-sectional surface area.

The device of the present invention preferably further comprises an outer cover encasing the first and second lumens and leaving both ends of the first lumen, the fluid inlet and the fluid outlet exposed.

A needle, including but not limited to a biopsy or amniocentesis needle, used in conjunction with the present invention is preferably longer than the rigid lumen.

The multi-lumen catheter of the present invention preferably further comprises a handle fixedly attached to the proximal end of the catheter offering the user increased control of the catheter.

In the form of an amniocentesis guide, the present invention preferably comprises a first rigid lumen adapted to extend across a bladder to guide and allow an amniocentesis needle to enter the amniotic sac through a wall of the bladder. The present invention further comprises a second lumen adapted to allow fluid to pass through the second lumen and fill the bladder.

In a preferred form, the catheter of the present invention comprises a first lumen having a proximal end and a distal end. The first lumen is adapted to project a needle from within the first lumen through the distal end. The catheter further comprises a second lumen having a proximal end and a distal end mounted parallel the first lumen and defining a fluid passageway extending from the proximal end of the second lumen through the wall of the second lumen proximate the distal end of the second lumen.

The method of the present invention is concerned with such tasks as obtaining amniotic fluid, performing transurethrovesical biopsies and obtaining other biological samples. The method of the present invention, in a general aspect, comprises filling a body cavity with a fluid and obtaining a biological sample while sonographically monitoring and guiding the sampling procedure through the cavity. In a preferred embodiment, the method comprises the steps of providing a multi-lumen catheter including a first rigid lumen having a first or proximal end suitable for receiving an amniocentesis or biopsy needle and having a second or distal end allowing the needle to project beyond the first lumen. A second lumen having a proximal fluid inlet and a distal fluid outlet is attached to the first lumen in parallel relationship having their proximal and distal ends in corresponding positions. An imaging device is positioned to allow imaging of a bladder, the associated uterus and the associated amniotic sac. The imaging device is preferably a sonographic transducer. The catheter may be inserted in the bladder, and fluid may be passed from the fluid inlet end and allowed to exit through the fluid outlet end filling the bladder and increasing sonographic visibility. The second end of the rigid lumen may now be seen more clearly and positioned against a wall of the bladder adjoining the uterus and amniotic sac. The amniocentesis or biopsy needle may now be inserted in the first end, through the first lumen, passed through the bladder wall and into the uterus. The needle may be further passed into the amniotic sac. Thus, amniotic fluid or another biological sample may now be aspirated through the needle.

In another preferred embodiment, the method of the present invention for obtaining a biological sample in transurethrovesical and other biosampling procedures comprises the steps of providing a multi-lumen catheter including a first rigid lumen having a first or proximal end suitable for receiving an amniocentesis, biopsy or other needle suitable for obtaining a biological sample and having a second or distal end allowing the needle to project beyond the first lumen. A second lumen having a proximal fluid inlet and a distal fluid outlet is attached to the first lumen in parallel relationship having their proximal and distal ends in corresponding positions. An imaging device is positioned to allow imaging of a body cavity through which the catheter is inserted and the associated target from which the biological sample is to be obtained. The imaging device is preferably a sonographic transducer. The catheter may be inserted in the body cavity, and the fluid may be passed from the fluid inlet end and allowed to exit through the fluid outlet end, filling the cavity and increasing sonographic visibility. The second end of the first lumen may now be seen more clearly and positioned within the body cavity proximate the target. The needle may now be inserted in the first end, through the first lumen and passed through a wall of the body cavity, if necessary, and into the target. The biological sample may now be aspirated through the needle.

A preferred method of the present invention provides for obtaining an amniotic fluid sample through a urethra and a bladder comprising the steps of filling the bladder with a fluid, passing a needle through the urethra and the bladder and obtaining an amniotic fluid sample while the bladder is so filled, and sonographically viewing the amniotic fluid sampling operation.

An additional preferred method of the present invention provides for obtaining a chorionic villus sample through a urethra and a bladder comprising the steps of filling the bladder with a fluid, passing a sampling device through the urethra and the bladder and obtaining a chorionic villus sample through the bladder while the bladder is so filled, and sonographically viewing the amniotic fluid sampling operation.

BRIEF DESCRIPTION OF THE DRAWINGS

FIG. 1 is a partially cutaway and sectioned double lumen catheter according to the present invention.

FIGS. 2 through 5a show placement of the catheter of FIG. 1 during various stages of a procedure of the present invention.

DETAILED DESCRIPTION OF THE PREFERRED EMBODIMENTS

Turning to FIG. 1, the multi-lumen catheter of the present invention is preferably double lumen catheter 10. Double lumen catheter 10 preferably includes first lumen 12 and second lumen 14 positioned in parallel relation First lumen 12 and second lumen 14 are surrounded about and along a portion of their shared length by outer cover 16. First lumen 12 preferably comprises material resistant to piercing by a needle, including but not limited to an amniocentesis or biopsy needle, and is rigid to serve as a guide for a needle. The rigidity of first lumen 12 imparts rigidity to catheter 10.

First lumen stylet 18 may be inserted in first lumen 12 through first lumen inlet 36. First lumen stylet 18 helps to reduce contamination of first lumen 12 which may result when first lumen 12 contacts a patient from whom the biological sample will be taken by restricting the entrance of material into first lumen 12 through first lumen exit orifice 20.

Fluid may be passed through second lumen 14 by passing the fluid through second lumen funnel inlet 30, second lumen funnel 28 and through flexible tubing 26 connected to second lumen 14. Fluid may exit second lumen 14 through second lumen exit orifice 22 positioned aside second lumen 14. Handle 24 allows the user to guide and better control catheter 10. Handle 24 is preferably located proximate first lumen inlet 36.

In use, first lumen stylet 18 may be removed from first lumen 12 by withdrawing first lumen stylet 18 through first lumen inlet 36. Needle 32 with needle stylet 40 inserted may then be inserted in first lumen 12. First lumen cone 42 may assist the user in guiding needle 32 into first lumen 12. Needle exit orifice 34 of needle 32 preferably may extend from first lumen exit orifice 20 a distance in the range of approximately two to eight centimeters when needle 32 is fully inserted in first lumen 12. Needle stylet 40 may be withdrawn from needle 32 through needle inlet 38 leaving needle exit orifice 34 open to allow biological samples to pass through needle exit orifice 34 into needle 32.

Turning now to FIG. 2, in a preferred embodiment, catheter 10, with first lumen stylet 18 positioned in first lumen 12, is inserted across bladder 104. This preferably positions second lumen exit orifice 22 within bladder 104 and positions first lumen exit orifice 20 against bladder wall 100 which adjoins uterus wall 102. Sonographic transducer 106 is shown positioned to afford the user a sonographic view of a portion of catheter 10 including first lumen exit orifice 20, a portion of bladder 104, bladder wall 100, uterus wall 102 and amniotic sac 200.

First lumen stylet 18 is preferably positioned within first lumen 12 during insertion of catheter 10 across bladder 104 to restrict the entrance of unwanted biological samples into first lumen 12. Because sonographic visibility is improved when viewing through fluid rather than air, sonographic visibility may be improved by filling bladder 104 with fluid. The fluid affords the user better visibility when positioning first lumen exit orifice 20 than would be available if the bladder were not filled with fluid.

Turning to FIG. 3, fluid, preferably a liquid, including but not limited to one or more of a mixture of a saline solution, water, an antiseptic solution, an antibacterial solution, and other solutions containing therapeutic properties, may be conveniently placed in bladder 104 by passing the fluid through funnel inlet 30, funnel 28, flexible tubing 26, and second lumen 14 so that the fluid quickly and efficiently exits through second lumen exit orifice 22 into bladder 104. Preferably, fluid may pass through second lumen 14 in a laminar flow. Second lumen exit orifice 22 is preferably positioned aside second lumen 14 allowing first lumen exit orifice 20 to be positioned against a surface such as bladder wall 100 while fluid is being discharged from second lumen exit orifice 22. Thus, the exiting fluid need not alter the position of catheter 10. Second lumen exit orifice 22 may be of size in the range of approximately 4 to 8 square millimeters in surface area.

The quantity of fluid placed in bladder 104 is preferably sufficient to fill bladder 104. The amount of fluid necessary to fill bladder 104 is typically in the range of about 200 to 400 cubic centimeters. First lumen stylet 18 positioned within first lumen 12 further serves to prevent fluid from exiting bladder 104 through first lumen 12.

Turning next to FIG. 4, to prevent fluid from exiting bladder 104 through second lumen 14, the path is restrictable. Surgical clamp 150 placed about flexible tubing 26 provides such a restriction. It will be understood that clamp 150 may be any clamping device suitable for restricting flow through flexible tubing 26. It will be further understood that any system suitable for restricting fluid flow from second lumen exit orifice 22 out through second lumen 14, including but not limited to a valve, a clip, a clamp, and a flow restricting device may be substituted for or used in addition to surgical clamp 150.

With the improved sonographic visibility provided by the fluid in bladder 104, a user may more accurately position first lumen exit orifice 20 against bladder wall 100. Preferably, after positioning catheter 10 across bladder 104 and positioning first lumen exit orifice 20 as desired, first lumen stylet 18 may be withdrawn from first lumen 12; and, needle 32, with needle stylet 40 preferably positioned within needle 32, may be placed in first lumen 12. First lumen cone 42 may assist the user in placing needle 32 in first lumen 12. Handle 24 allows the user to control the positioning of catheter 10.

When catheter 10 is properly positioned for an amniocentesis, first lumen exit orifice 20 is preferably positioned against bladder wall 100 allowing needle 32 to be passed along and through first rigid lumen 12 so as to extend out from first lumen exit orifice 20 piercing bladder wall 100 and uterus wall 102 and positioning needle exit orifice 34 in amniotic sac 200. The improved sonographic visibility provided by the fluid placed in bladder 104 through second lumen 14 provides the user greater visibility of amniotic sac 200 and fetus 204. The improved sonographic visibility increases the likelihood of properly positioning needle 32 to pass into amniotic sac 200 and reduces the likelihood of accidentally striking fetus 204 with needle exit orifice 34.

The improved sonographic visibility further increases the likelihood of properly positioning needle 32, or other sampling device, for other biological sampling procedures including but not limited to chorionic villus sampling. Additionally, control of the position of needle 32 is provided by first lumen 12. First lumen 12 is resistant to piercing by needle 32 and is rigid thus containing and guiding needle 32.

Needle stylet 40, which is preferably positioned within needle 32 when needle 32 is placed in first lumen 12 and when needle 32 is thrust through bladder wall 100, uterus wall 102 and into amniotic sac 200, restricts the entrance of undesired biological samples into needle 32.

Turning to FIGS. 5 and 5a, needle stylet 40 is withdrawn from needle 32 and needle exit orifice 34 remains positioned in amniotic sac 200 allowing amniotic fluid 202 to be withdrawn through needle exit orifice 104. Syringe 160 is attached to needle inlet 38 and amniotic fluid is aspirated through needle 32 into syringe 160.

Second lumen 14 and second lumen exit orifice 22 preferably remain positioned in bladder 104 while amniotic fluid is being withdrawn. First lumen 12 and first lumen exit orifice 20 also preferably remain in bladder 104 with first lumen exit orifice preferably remaining positioned against or near bladder wall 100 where bladder wall 100 adjoins uterus 152 and uterus wall 102. After a sample of amniotic fluid 202 is aspirated, needle 32 is preferably withdrawn from first lumen 12 and catheter 10 is preferably withdrawn from bladder 104.

Turning again to FIG. 1, first lumen 12 is preferably attached to second lumen 14 in parallel relationship. In a preferred embodiment, first lumen 12 and second lumen 14 are in parallel relationship and are abutting along a portion of their length This preferred embodiment allows the user precision in viewing first lumen 12 directly in a sonographic image. In another preferred embodiment, first lumen 12 and second lumen 14 are in a parallel relationship wherein second lumen 14 is coaxial to first lumen 12 with first lumen 12 preferably positioned substantially central to second lumen 14.

First lumen 12 is preferably constructed of stainless steel, rigid rubber or rigid plastic Surgical quality stainless steel is not required.

Second lumen 14 is preferably constructed of plastic or rubber, preferably having a minimal tendency to irritate tissue. Second lumen 14 passes fluid.

Outer cover 16 preferably comprises a pliable material to aid in insertion of catheter 10 across bladder 104 or other body cavities Outer cover 16 preferably comprises plastic or rubber, preferably having a minimal tendency to irritate tissue.

In still another preferred embodiment, second lumen 14 is integral to outer cover 16.

It will be apparent to one skilled in the art that the present invention may be inserted in other body cavities, including, but not limited to, the ear, the mouth, the pharynx, the chest including, but not limited to the plural cavity, the abdominal cavity and the rectum for biosampling targets proximate the cavity. The cavity is preferably filled with fluid passed through the second lumen and a biological sample is preferably obtained through a sampling device extending from the distal end of the first lumen.

As will also be apparent to one skilled in the art, the present invention enables biological sampling utilizing sampling devices including, but not limited to, needles, including but not limited to amniocentesis and biopsy needles, other tube shaped sampling devices, forceps, including but not limited to biopsy forceps, and curettes. The sampling devices described are merely descriptive of some of the many sampling devices known in the art and are not intended as limitations.

As will be further apparent to one skilled in the art, the introduction of the present invention into certain body cavities may be assisted where the distal end of catheter 10 is sharpened. Entry into closed body cavities may be assisted by a sharpened distal end of catheter 10.

A plurality of sizes of catheter 10, as would be apparent to one skilled in the art, may be chosen to correspond to a plurality of sizes of body cavities. The plurality of sizes of catheter 10 enable insertion of catheter 10 in correspondingly sized body cavities.

Further modifications and alternative embodiments of the apparatus and the method of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size and arrangement of parts. For example, equivalent elements and materials may be substituted for those illustrated and described herein. Parts may be reversed, and certain features of the invention may be utilized independently of the use of other features all as will be apparent to one skilled in the art after having the benefit of this description of the invention.

I claim:

1. A multi-lumen catheter comprising:
   an amniocentesis needle;
   a first rigid lumen having a first end and a second end, said first end having a first orifice for receiving said needle and said second end having a second orifice opposite said first orifice to enable said needle to exit the second end of said first lumen; and
   a second lumen having a fluid inlet and a fluid outlet; said first lumen being attached to said second lumen in parallel relationship, said first end being in proximal relation to said fluid inlet, and said second end being in proximal relation to said fluid outlet.

2. The multi-lumen catheter of claim 1 wherein said needle is of length greater than that of said first lumen.

3. A multi-lumen catheter comprising:
   a biopsy needle;
   a first rigid lumen having a first end and a second end, said first end having a first orifice for receiving said needle and said second end having a second orifice opposite said first orifice to enable said needle to exit the second end of said first lumen; and
   a second lumen having a fluid inlet and a fluid outlet; said first lumen being attached to said second lumen in parallel relationship, said first end being in proximal relation to said fluid inlet, and said second end being in proximal relation to said fluid outlet.

4. A method of obtaining amniotic fluid comprising the steps of:
   providing a multi-lumen catheter including a first rigid lumen having a first end suitable for receiving an amniocentesis needle and having a second end allowing such a needle to exit said first lumen, a second lumen having a fluid inlet and a fluid outlet, said second lumen being attached to said first lumen in parallel relationship having said first end in proximal relation to said fluid inlet and having said second end in proximal relation to said fluid outlet;
   positioning an imaging device to allow imaging of a bladder, an associated uterus and an associated amniotic sac;
   inserting said multi-lumen catheter in said bladder;
   passing fluid into said fluid inlet and allowing fluid to exit through said fluid outlet and fill said bladder;
   positioning said second end against a wall of said bladder adjoining said uterus and said amniotic sac;
   inserting an amniocentesis needle in said first end, through said first lumen and into said amniotic sac; and
   aspirating amniotic fluid through said needle.

5. The method of claim 4 wherein said imaging device comprises a sonographic transducer.

6. A method of performing a transurethrovesical biopsy comprising the steps of:
   providing a multi-lumen catheter including a first rigid lumen having a first end suitable for receiving a biopsy needle and having a second end allowing such a needle to exit said first lumen, a second lumen having a fluid inlet and a fluid outlet, said second lumen being attached to said first lumen in parallel relationship having said first end in proximal relation to said fluid inlet and having said second end in proximal relation to said fluid outlet;
   positioning an imaging device to allow imaging of a bladder and an associated target;
   inserting said multi-lumen catheter in said bladder;
   passing fluid into said fluid inlet and allowing fluid to exit through said fluid outlet and fill said bladder;
   positioning said second end against a wall of said bladder proximate said target;
   inserting a biopsy needle in said first end, through said first lumen and into said target; and
   aspirating a biological sample through said needle.

7. A method of obtaining an amniotic fluid sample through a urethra and a bladder comprising the steps of:
   filling said bladder with a fluid;
   passing a needle through said urethra and said bladder and obtaining said amniotic fluid sample while said bladder is so filled; and
   sonographically viewing said amniotic fluid sampling operation.

8. A method of obtaining a chorionic villus sample through a urethra and a bladder comprising the steps of:
   filling said bladder with a fluid;
   passing a sampling means through said urethra and said bladder and obtaining said chorionic villus sampling while said bladder is so filled; and
   sonographically viewing said chorionic villus sampling operation.

9. A method of obtaining a biological sample comprising the steps of:
   providing a multi-lumen catheter including a first rigid lumen having a first end suitable for receiving a needle and having a second end allowing such a needle to exit said first lumen, a second lumen having a fluid inlet and a fluid outlet, said second lumen being attached to said first lumen in parallel relationship having said first end in proximal relation to said fluid inlet and having said second end in proximal relation to said fluid outlet;
   positioning an imaging device to allow imaging of a body cavity and an associated target;
   inserting said multi-lumen catheter in said body cavity;

passing fluid into said fluid inlet and allowing fluid to exit through said fluid outlet and fill said cavity;

positioning said second end within said cavity and proximate said target;

inserting a needle in said first end, through said first lumen and into said target; and aspirating a biological sample through said needle.

10. The method of claim 24 wherein said imaging device comprises a sonographic transducer.

* * * * *

UNITED STATES PATENT AND TRADEMARK OFFICE
CERTIFICATE OF CORRECTION

PATENT NO. : 5,147,335

DATED : 09/15/92

INVENTOR(S) : Jeffrey Wright

It is certified that error appears in the above-identified patent and that said Letters Patent is hereby corrected as shown below:

On the title page,

In the abstract, line 1, delete "metehod" and insert --method--

In claim 8, line 51, column 8, delete "sampling" and insert --sample--

In claim 10, line 4, column 10, delete "24" and insert --9--

Signed and Sealed this

Second Day of November, 1993

Attest:

BRUCE LEHMAN

*Attesting Officer*   *Commissioner of Patents and Trademarks*